US00PP23510P2

(12) United States Plant Patent
Hanes

(10) Patent No.: US PP23,510 P2
(45) Date of Patent: Apr. 2, 2013

(54) ***PETUNIA* PLANT NAMED 'PEHY0002'**

(50) Latin Name: *Petunia hybrida*
Varietal Denomination: PEHY0002

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 2 days.

(21) Appl. No.: 13/317,384

(22) Filed: Oct. 17, 2011

(51) Int. Cl.
*A01H 5/00* (2006.01)

(52) U.S. Cl. ..... Plt./356.19

(58) Field of Classification Search ..... Plt./356.19
See application file for complete search history.

*Primary Examiner* — Annette Para
(74) *Attorney, Agent, or Firm* — Joshua L. Price

(57) ABSTRACT

A new *Petunia* plant named 'PEHY0002' particularly distinguished by the small bold purple flowers, good floriferousness, medium green foliage, good branching, initially semi-compact and then outwardly spreading plant habit, with early flowering.

1 Drawing Sheet

Latin name of the genus and species of the plant claimed: *Petunia hybrida.*

Varietal denomination: 'PEHY0002'.

BACKGROUND OF THE NEW PLANT

The present invention comprises a new *Petunia*, botanically known as *Petunia hybrida*, and hereinafter referred to by the variety name 'PEHY0002'.

'PEHY0002' is a product of a planned breeding program. The new cultivar has small bold purple flowers, good floriferousness, medium green foliage, good branching, initially semi-compact and then outwardly spreading plant habit, with early flowering.

'PEHY0002' originated from a hybridization made in August 2007 in a controlled breeding environment in Gilroy, Calif. The female parent was the proprietary, unpatented plant designated as '1789-2', with a lighter amethyst color, more trailing habit and is later to flower.

The male parent of 'PEHY0002' is a commercially available variety identified as 'Pic Rossa', U.S. Plant Pat. No. 25,199, with pinkish-rose color, more upright habit, more vigorous, and is earlier to flower. The resultant seed was sown in December 2007.

'PEHY0002' was selected as one flowering plant within the progeny of the stated cross in the March 2008 in a controlled environment in Gilroy, Calif.

The first act of asexual reproduction of 'PEHY0002' was accomplished when vegetative cuttings were propagated from the initial selection in March 2008 in a controlled environment in Gilroy, Calif.

BRIEF SUMMARY OF INVENTION

Horticultural examination of plants grown from cuttings of the plant initiated in March 2008, and continuing thereafter, has demonstrated that the combination of characteristics as herein disclosed for 'PEHY0002' are firmly fixed and are retained through successive generations of asexual reproduction.

'PEHY0002' has not been observed under all possible environmental conditions. The phenotype may vary significantly with variations in environment such as temperature, light intensity and day length.

Plant Breeder's Rights for this cultivar were applied for in Canada on Dec. 17, 2010, #10-7131 and in the Community Plant Variety Office on Oct. 15, 2010, #2010/2183. 'PEHY0002' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
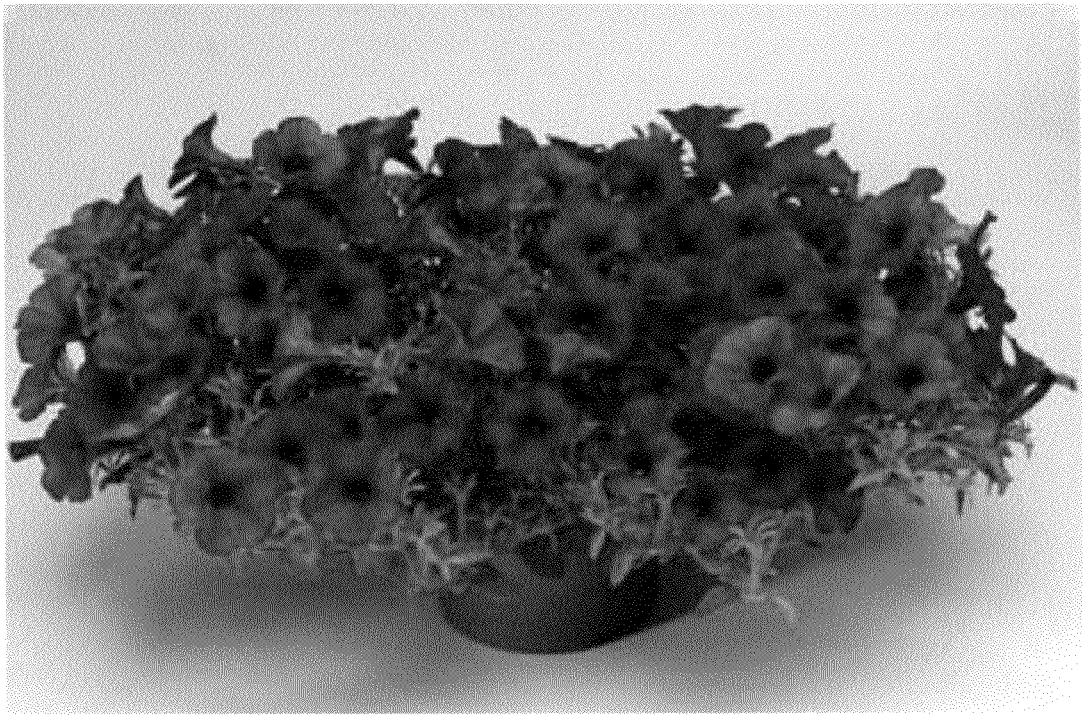
Figure 2:
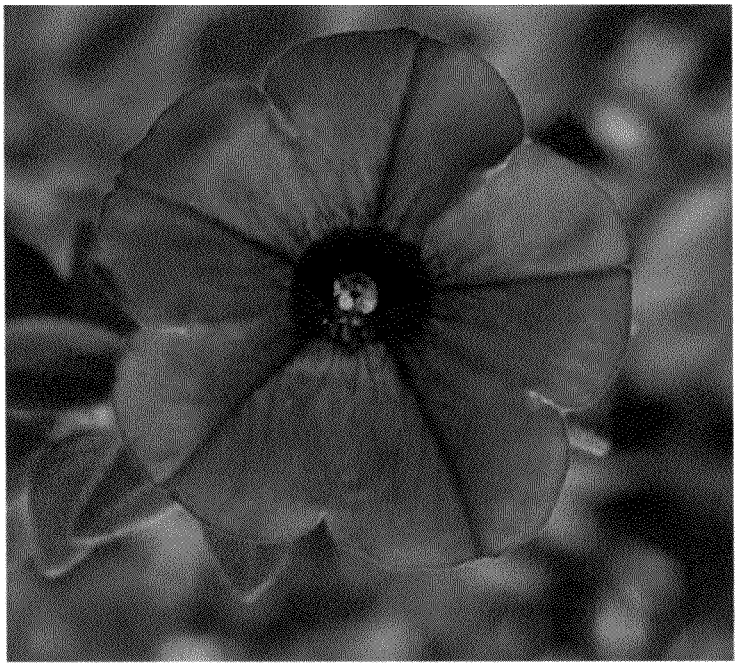

The accompanying photographic drawing shows typical flower and foliage characteristics of 'PEHY0002' with colors being as true as possible with an illustration of this type. The photographic drawing shows in FIG. 1, a flowering plant of the new variety, and a close-up of the flowers in FIG. 2.

DETAILED BOTANICAL DESCRIPTION

The aforementioned photographs were taken in the spring of 2010 from plants grown in a greenhouse trial in Enkhuizen, The Netherlands. These plants were growing in 12 cm pots and were approximately 12-14 weeks of age.

The plant descriptions and measurements were taken in Gilroy, Calif. in late April 2011 from plants grown in a breeder trial in the greenhouse. Plants were grown in 4.5 inch pots and were approximately 10 weeks of age.

Color references are made to The Royal Horticultural Society Colour Chart (R.H.S.) 2001.

TABLE 1

DIFFERENCES BETWEEN THE NEW VARIETY 'PEHY0002' AND A SIMILAR VARIETY

| | 'PEHY0002' | 'PIC AMTHE' (U.S. Plant patent application No. 12/657,237) |
|---|---|---|
| Flower color: | Purple-violet | Purple |
| Flowering color: | Fades less | Fades more |
| Foliage color: | Medium green | More yellow-green |
| Foliage size: | Little smaller | Little larger |

Plant:

*Form, growth and habit.*—Compact habit, good branching, early flowering.

*Plant height.*—5.0 cm.

*Plant height (inflorescence included).*—8.0-10.0 cm.

*Plant width.*—50.0-55.0 cm.

Roots:

*Number of days to initiate roots and produce a rooted cutting.*—About 18-23 days at about 22 degrees C.

*Type.*—Fine, fibrous, free branching.

*Color.*—RHS N155B but whiter.

Foliage:

*Arrangement.*—Alternate, upper leaves sub-opposite.

*Immature, leaf color, upper surface.*—Closest to RHS 137B, slightly darker at apex.

*Lower surface.*—Closest to RHS 137C.

*Mature, leaf color, upper surface.*—Closest to RHS 137B, slightly darker at apex.

*Lower surface.*—Closest to RHS 137C.

*Length.*—2.0-2.5 cm.

*Width.*—0.9-1.1 cm.

*Shape.*—Elliptical.

*Base shape.*—Acuminate.

*Apex shape.*—Obtuse.

*Margin.*—Entire.

*Texture, upper surface.*—Hirsute; few glandular hairs.

*Lower surface.*—Hirsute; few glandular hairs.

*Color of veins, upper surface.*—RHS 144B; indistinct in upper portion.

*Color of veins, lower surface.*—RHS 144B; indistinct in upper portion.

*Petiole color.*—RHS 144B.

*Length.*—0.2-0.3 cm.

*Diameter.*—0.15-0.2 cm.

*Texture.*—Hirsute; few glandular hairs.

Stem:

*Color of stem.*—Closest to RHS 144A.

*Length of stem.*—25.0-33.0 cm.

*Diameter.*—0.2 cm.

*Length of internodes.*—0.7-1.6 cm.

*Texture.*—Pilose; few glandular hairs.

*Color of peduncle.*—RHS 144A.

*Length of peduncle.*—3.2-4.7 cm.

*Peduncle diameter.*—0.1 cm.

*Texture.*—Pilose; few glandular hairs.

Inflorescence:

*Type.*—Flowers appear solitary in upper leaf axis. Floret type: Funnel-shaped; 5 lobed petals; fused at the base; calyx, 5 deeply lobed sepals.

*Blooming habit.*—Continuous throughout the growing season, with good floriferousness.

*Quantity of inflorescences per plant.*—Approximately 150 and many more buds.

*Lastingness of individual blooms on the plant.*—5-7 days.

*Fragrance.*—None.

Bud (just before opening/showing color):

*Color.*—RHS N186C.

*Length.*—2.2-2.5 cm.

*Width.*—0.5-0.7 cm.

*Shape.*—Oblong.

Immature inflorescence:

*Diameter.*—2.8-3.1 cm.

*Color, upper surface.*—Closest to RHS N81A but darker, more velvety looking.

*Lower surface.*—Between RHS N81B and RHS N81C but much greyer.

Mature inflorescence:

*Floret horizontal diameter.*—3.5-4.0 cm.

*Vertical depth.*—3.2-3.5 cm.

*Petal color, upper surface.*—Closest to RHS N81A maturing to slightly lighter hue.

*Lower surface.*—Between RHS 81B and RHS 81C but greyer.

*Petal apex shape.*—Very slightly retuse.

*Petal base shape.*—Fused.

*Petal margin.*—Entire.

*Waviness of petals.*—Moderate.

*Petal lobation.*—Moderate.

*Petal texture, upper surface.*—Papillose.

*Under surface.*—Pilose; few glandular hairs.

*Corolla tube color inside.*—Ground color closest to RHS 79B and heavily overlaid with RHS N186B veining and midveins.

*Outside.*—Closest to RHS N79B but less red hues; lighter than RHS N186B veining and RHS N186B midveins.

*Corolla tube length.*—2.3-2.5 cm.

*Corolla texture outside.*—Pilose; few glandular hairs.

*Inside.*—Papillose.

Calyx:

*Color, outer surface.*—Closest to RHS 144A but slightly more green.

*Inner surface.*—Closest to RHS 137C.

*Length.*—1.0-1.1 cm.

*Width.*—0.15-0.2 cm.

*Shape.*—Oblong.

*Apex shape.*—Obtuse.

*Base.*—Fused.

*Margins.*—Entire.

*Texture, upper surface.*—Glabrous; few glandular hairs.

*Lower surface.*—Pilose; few glandular hairs.

Reproductive organs:

*Pistil.*—1.

*Length.*—1.5 cm.

*Style color.*—RHS N144D basally and closest to RHS 86A upper but greyer.

*Style length.*—1.3-1.4 cm.

*Stigma color.*—RHS N187A.

*Ovary color.*—RHS 144B with RHS 144A apex.

*Stamens.*—4-5.

*Color of filaments.*—RHS N144D basally with RHS N80A upper half.

*Length filaments.*—0.7-0.9 cm.

*Anther color.*—Mostly RHS N155D with a hint of purple.

*Anther length.*—0.15 cm.

*Anther shape.*—Oval.

*Color of pollen*.—Between RHS N187B and RHS N187C.

*Pollen amount*.—Moderate.

*Fertility/seed set*.—Has not been observed on this hybrid.

*Disease/pest resistance*.—Has not been observed on this hybrid.

What is claimed is:

1. A new and distinct variety of *Petunia* plant named 'PEHY0002' substantially as illustrated and described herein.

* * * * *